(12) United States Patent
Wallace et al.

(10) Patent No.: US 10,561,605 B2
(45) Date of Patent: Feb. 18, 2020

(54) ELECTROSPUN THERAPEUTIC CARRIER AND IMPLANT

(71) Applicants: Robert F. Wallace, Fort Myers, FL (US); Matthew Q. Shaw, Carmel, IN (US)

(72) Inventors: Robert F. Wallace, Fort Myers, FL (US); Matthew Q. Shaw, Carmel, IN (US)

( * ) Notice: Subject to any disclaimer, the term of this patent is extended or adjusted under 35 U.S.C. 154(b) by 557 days.

(21) Appl. No.: 14/161,614

(22) Filed: Jan. 22, 2014

(65) Prior Publication Data

US 2014/0205645 A1 Jul. 24, 2014

Related U.S. Application Data

(60) Provisional application No. 61/755,457, filed on Jan. 22, 2013.

(51) Int. Cl.
*A61K 9/00* (2006.01)

(52) U.S. Cl.
CPC .................... *A61K 9/0024* (2013.01)

(58) Field of Classification Search
None
See application file for complete search history.

(56) References Cited

U.S. PATENT DOCUMENTS

| | | | |
|---|---|---|---|
| 5,989,579 A | 11/1999 | Darougar et al. | |
| 6,251,090 B1 | 6/2001 | Avery et al. | |
| 6,589,225 B2 | 7/2003 | Orth et al. | |
| 7,582,080 B2 | 9/2009 | Santini et al. | |
| 7,794,490 B2 | 9/2010 | King | |
| 7,824,699 B2 | 11/2010 | Raloh et al. | |
| 7,892,221 B2 | 2/2011 | Santini, Jr. et al. | |
| 2003/0069560 A1* | 4/2003 | Adamis | A61F 9/0017 604/521 |
| 2004/0254317 A1 | 12/2004 | Hu et al. | |
| 2005/0014252 A1* | 1/2005 | Chu | A61K 35/32 435/325 |
| 2006/0085063 A1* | 4/2006 | Shastri | A61F 2/02 623/1.41 |
| 2007/0043428 A1* | 2/2007 | Jennings | A61L 31/10 623/1.15 |
| 2007/0207186 A1* | 9/2007 | Scanlon | A61F 2/07 424/424 |
| 2007/0275458 A1 | 11/2007 | Gouma | |
| 2009/0130301 A1 | 5/2009 | Bahnmuller et al. | |
| 2009/0208577 A1 | 8/2009 | Xu et al. | |
| 2009/0246259 A1 | 10/2009 | Kita et al. | |
| 2011/0229551 A1 | 9/2011 | Doshi et al. | |
| 2012/0040581 A1 | 2/2012 | Kim | |

OTHER PUBLICATIONS

Agarwal et al. (Use of electrospinning technique for biomedical applications, Polymer, 2008, vol. 49, p. 5603-5621).*

* cited by examiner

*Primary Examiner* — Bethany P Barham

(74) *Attorney, Agent, or Firm* — Rathe Lindenbaum LLP

(57) ABSTRACT

A biodegradable therapeutic carrier and implant comprises a layer of biodegradable electrospun material and floored wells formed by the layer to contain therapeutic.

21 Claims, 10 Drawing Sheets

ELECTROSPUN THERAPEUTIC CARRIER AND IMPLANT

CROSS-REFERENCE TO RELATED PATENT APPLICATIONS

The present application claims priority under 35 USC 120 from co-pending U.S. Provisional Patent Application Ser. No. 61/755,457 filed on Jan. 22, 2013 by Wallace et al. and entitled ELECTROSPINNING, the full disclosure of which is hereby incorporated by reference.

BACKGROUND

Therapeutics, vaccines, medicines and drugs (collectively referred to as therapeutics) are sometimes administered in liquid form via shots. In other circumstances, such therapeutics are delivered orally in the form of pills. In some circumstances, therapeutics are delivered via implants. Such therapeutic delivery systems are often complex and difficult to manufacture or are difficult to precisely control a timed release of different therapeutics.

DETAILED DESCRIPTION OF THE EXAMPLE EMBODIMENTS

Figure 1:
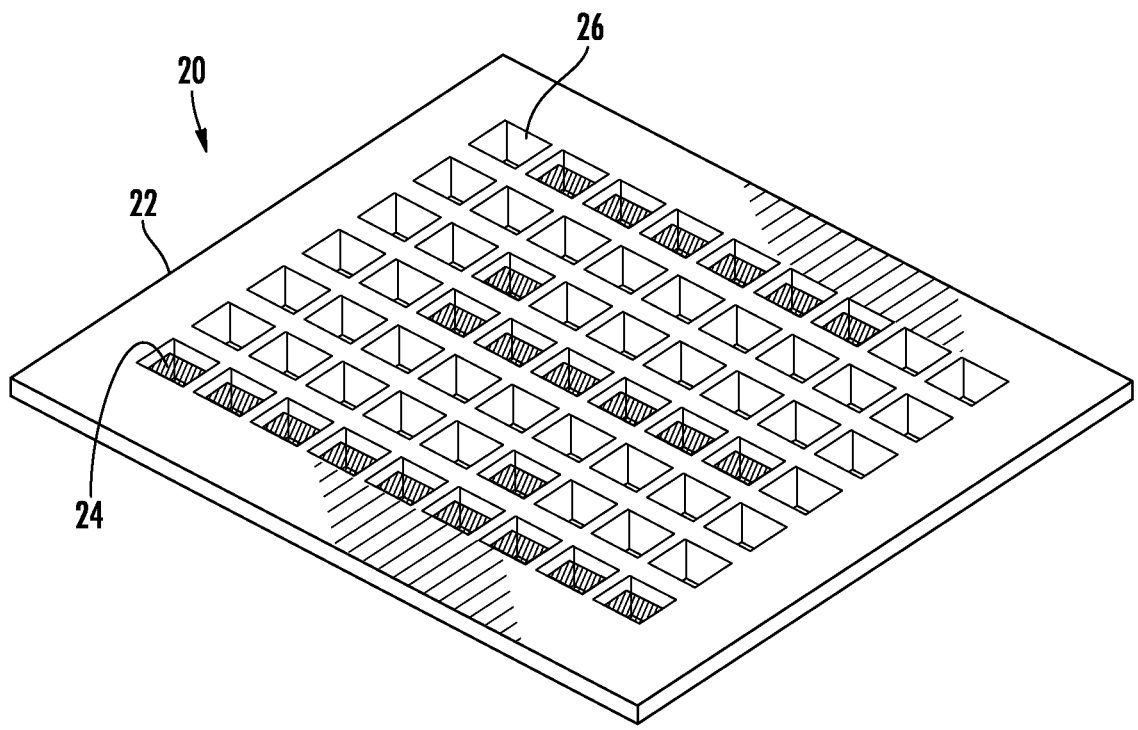
FIG. 1 is a top perspective view of an example electrospun therapeutic carrier filled with therapeutic masses.

FIG. 1 illustrates an example therapeutic implantable device 20. Therapeutic implantable device 20 is configured to be implanted via needle into a patient, such as a person or animal, for timed release of one of more therapeutics. As will be described hereafter, device 20 delivers or releases therapeutics in a precisely controlled time fashion using a less complex and more easily manufactured delivery structure. Therapeutic implantable device 20 comprises therapeutic carrier 22 and therapeutic masses 24.

Therapeutic carrier 22 comprises a layer of biodegradable material formed from biodegradable electrospun fibers. Examples of biodegradable materials from which therapeutic carrier 22 is formed include but are not limited to, a cellulose, or variants thereof, glycolic acid derived membranes or other materials forms, or their combinations, with characteristics such that the materials are biodegradable naturally and completely in the host body The degradation may be time controlled by two factors: the nature and amount of the material forming therapeutic carrier 22. Because therapeutic carrier 22 is formed by electrospinning, the thickness of therapeutic carrier 22 may be precisely controlled at the microscale or nanoscale level.

As shown by FIG. 1, level 22 comprises wells 26. Each of wells 26 forms a basin having a floor and sidewalls that define a chamber or cavity receiving a therapeutic mass 24. Although wells 26 are illustrated as being arranged in a 7×9 rectangular array or grid of cells, in other implementations, wells 26 may be divided differently sized arrays have a rectangular or other shapes. Although wells 26 are each illustrated as being rectangular, in other implementations, wells 26 may have other shapes.

Therapeutic masses 24 comprise individual portions of therapeutics loaded or deposited into individual cells 26 of therapeutic carrier 22. Therapeutic masses 50 comprise medicinal materials supported or carried by carrier 22. Examples of therapeutic masses 50 include, but are not limited to, pharmaceuticals (chemotherapy agents, antibiotics, antiviral agents, anti-hypertension agents, vassodilatation agents, vasoconstriction agents, local anesthetics, NSAIDA, steroids, psychotropic agents, neurotropic agents), proteins (including antibodies, interferons and hormones, peptides (interleukins, RNA's) osteogenic and osteolytic agents, genetic altering agents and stem cells. Such therapeutics may be solid, semi-liquid or liquid.

In one implementation, each of therapeutic masses 24 may constitute the same therapeutic formulation in generally the same doses. In other implementations, some of therapeutic masses 24 may be different formulations or different doses of the same therapeutic formulation. For example, one of wells 26 may contain a first therapeutic mass 24 of a first type while another wells 26 may contain a different type of therapeutic. In one implementation, each of wells 26 contains a therapeutic mass 24. In other implementations, the number and location of wells 24 containing a therapeutic mass 26 may be varied to provide a customized release (dosage and/or timing) of therapeutics for different patients or persons. In short, therapeutic carrier 22 provides a biodegradable therapeutic carrier which is customizable for different patients having different dosage requirements and different therapeutic time release itineraries. Because therapeutic carrier 22 is formed by electrospinning, the dimension of wells 26 as well as the thickness of the walls and floor of wells 26 may be precisely controlled to precisely control the rate at which therapeutic carrier 22 about individual wells biodegrade before releasing the contain therapeutic mass 24.

In one implementation, the electrospun fibers forming therapeutic carrier 22 themselves incorporate one or more therapeutics. In one implementation, therapeutic carrier 22 may be immersed within a therapeutic bath, wherein the fibers of therapeutic carrier 22 absorb the one or more therapeutics. In another implementation, therapeutics may be applied to the fibers prior to the fibers forming therapeutic carrier 22 such as prior to the fibers being deposited upon a charged collector plate utilized in the electrospinning of therapeutic carrier 22. In yet another implementation, therapeutics may be combined with the biodegradable material and solvent forming the liquid which is subsequently electrospun into the fibers that form therapeutic carrier 22.

Figure 2:
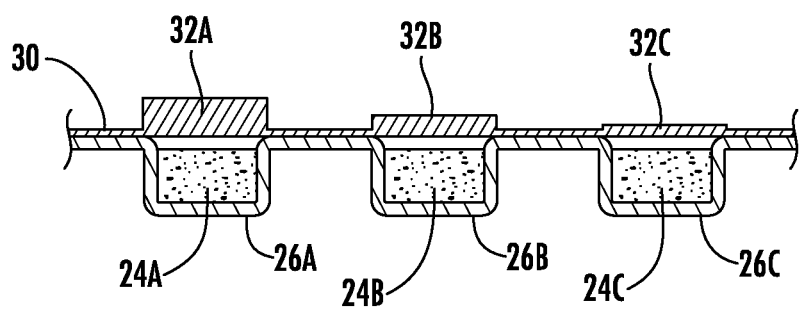
FIG. 2 is a sectional view of a portion of the therapeutic carrier FIG. 1 sealed with an example capping layer.

Upon loading of therapeutic masses 24 into wells 26, the cavities of wells 26 and the contained therapeutic masses 24 are sealed. In one implementation, a capping layer is laminated across therapeutic carrier 22 over each of wells 26. FIG. 2 is a sectional view of a portion of therapeutic carrier 22 and therapeutic masses 24 sealed by a capping layer 30. In the example illustrated, capping layer 30 has a non-uniform thickness. In particular, portions of capping layer 30 opposite to corresponding wells 26 have different thicknesses to control the timing at which such portions biodegrade to a point that the therapeutic contained within the corresponding well is released. In the example illustrated, capping layer 30 comprises a first portion 32A opposite a first well 26A containing a first therapeutic 24A, a second portion 32B opposite a second well 26B containing a second therapeutic 24B (different and therapeutic 24A), and a third portion 32C opposite a third well 26C containing the first therapeutic 24A. portions 32A, 32B and 32C each have a different thickness with portion 32A having the greatest thickness and portion 32C having the least thickness. In one implementation, this different than thickness results in therapeutic 24A of well 26A being first released, therapeutic 24B of well 26B being released next and therapeutic 24C of well 26C being released last.

Although the difference in thicknesses exaggerated for purposes of illustration, in some implementations, the thickest of such portions opposite to wells 26 is still thinner than the walls of well 26 such that release of the therapeutic is controlled based upon the thickness of such portions of capping layer 30. In yet other implementations, the thickness of the walls (floors and sidewalls) of each well 26 are also varied similar to the thickness of the corresponding overlying portions of capping layer 30 such that the walls of each well 26 and its corresponding overlying capping portion 32 biodegrade to the point of releasing the contained therapeutic through both the wall the well and capping layer 30 at approximately the same time. In still other implementations, the thickness of the walls of wells 26 are such that the walls of wells 26 biodegrade sooner than opposing portions of capping layer 30 such that the release of therapeutics is controlled by the varying controlled thickness of the walls of the different wells 26.

In one implementation, capping layer 30 comprises a distinct homogenous layer which is laminated, glued or otherwise adhered to therapeutic carrier 22 over wells 26. In yet another implementation, Layer 30 is composed of multiple independent caps that are individually laminated or otherwise joined and secured to therapeutic carrier 22 across one or more corresponding wells 26 of therapeutic carrier 22. An individual cap may seal and cover a single well 26 or a group of wells 26.

In one implementation, capping layer 30 is formed by electrospinning Because capping layer is formed by electrospinning, the thickness of different portions 32 of capping layer 30 they be precisely controlled. In one implementation, capping layer 30 is formed from electrospun fibers that incorporate, are impregnated or are coated with a therapeutic such that as layer 30 itself biodegrades, therapeutics are released. For example, in one implementation, the therapeutic may be combined with the solvent in the biodegradable material that form the liquid that is formed into fibers by electrospinning. In another implementation, the therapeutic may be sprayed or otherwise applied to the electrospun fiber prior to the electrospun fiber being deposited upon a collector plate and forming capping layer 30. In yet another implementation, the capping layer 30 may be soaked otherwise coated with the therapeutic, wherein the mesh of nonwoven electrospun fibers absorb the therapeutic for subsequent time to release during biodegradation of capping layer 30.

Figure 3:
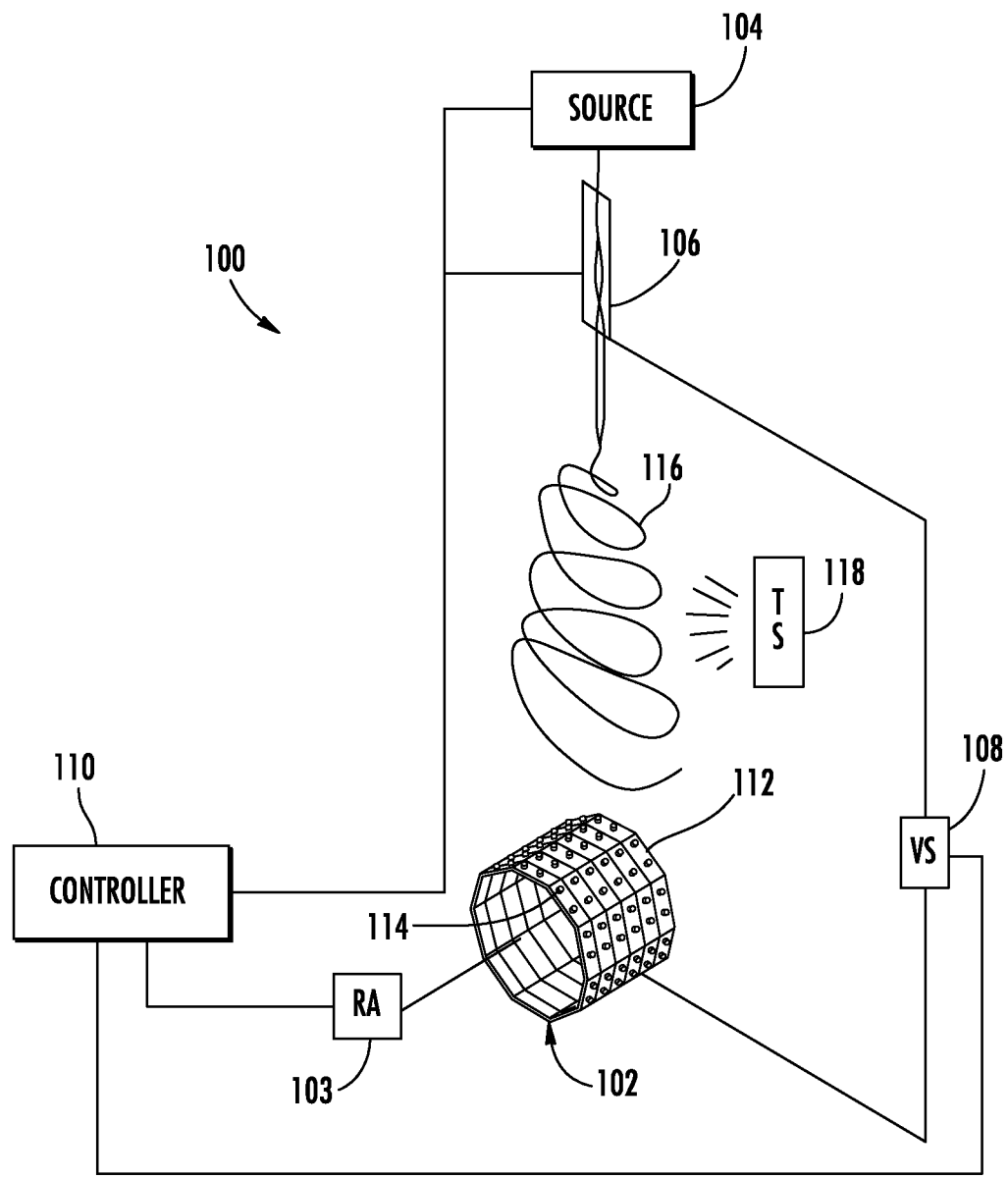
FIG. 3 is a schematic diagram of an example electrospinning system for forming a therapeutic carrier.

FIG. 3 schematically illustrates electrospinning system 100 for forming electrospun therapeutic carrier, such as carrier 22. Electrospinning system 100 comprises collector 102, rotary actuator 103, material source 104, syringe or nozzle 106, voltage source 108 and controller 110. Collector 102 comprises an electrically conductive structure upon which electrospun therapeutic carrier, such as carrier 22, is formed. In the example illustrated, collector 102 comprises a polygonal cylinder configured to be rotationally driven by rotary actuator 103. Collector 102 comprises a plurality of interconnected collector plates providing facets or faces 112, wherein each face 112 comprises sunken depressions or recesses 114 or raised protruberances or projections 114. The recesses 114 and/or projections 114 provide the nonwoven mesh of electrospun fibers 116 that are deposited upon collector 102, with wells 26. Although each face 112 is illustrated as including a 2×6 array of recesses or projections for forming a corresponding 2×6 array of wells 26, in other implementations, faces 112 may include a greater or fewer of such recesses or projections for forming a corresponding greater or fewer of such wells 26. Because collector 102 comprises a polygonal cylinder, collector 102 may be continuously rotationally driven as fibers 116 are deposited upon carrier 102 for mass production of therapeutic carriers such as carrier 22. In other implementations, collector 102 may alternatively comprise a single planar or flat plate having recesses 114 or projections 114 for forming wells 26.

Material source 104 comprises a source of material for being formed upon collector 102 by Electrospinning Material source 104 comprise a container of a biodegradable base material such as a biodegradable polymer. Examples of such biodegradable polymers include but are not limited to, poly-(lactide) (PLA), poly (.epsilon.-caprolactone), polyethylene oxide, poly(L-lactide-co-.epsilon.-caprolactone) and poly-(lactide-co-glycolide) (PLGA). Non-biodegradable synthetic polymers such as nylon 4,6; nylon 6; nylon 6,6; nylon 12; polyacrylic acid; polyacrylonitrile; poly(benzimidazol (PBI); polycarbonate; poly(etherimide), PEI; poly (ethylene terephthalate); polymethylmethacrylate; polystyrene; polysulfone; poly(urethane); poly(urethane urea)s; poly(vinyl alcohol); poly(N-vinylcarazole); poly(vinyl chloride); poly(vinyl pyrrolidone); poly(vinylidene fluoride) (PVDF); and hydrogels such as galyfilcon and silicone hydrogels.

In one implementation, material source 104 may additionally include one or more therapeutics and associated solvents. In such an implementation, the therapeutics and associated solvents are mixed in the liquid biodegradable base material or biodegradable polymer such that the fibers 116 formed from material source 104 comprise both the biodegradable base material and the therapeutic. In one of limitation, the solvent evaporates in the formation of fibers 116.

Nozzle 106 receives the electrospinning material from source 104. Nozzle 106 ejection supplies material from source 104 and is electrically charged with respect to collector 102 to form fibers 116. Voltage source 108 comprises a source of voltage or electric charge for placing nozzle 106 and collector 102 at different electrical potentials.

Controller 110 comprises one or more processing units under the direction of instructions provided by a non-transitory computer readable medium. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 110 may be embodied as part of one or more application-specific integrated circuits (ASICs). Unless otherwise specifically noted, the controller is not limited to any specific combination of hardware circuitry and software, nor to any particular source for the instructions executed by the processing unit.

Controller 110 controls the operation of material source 104, nozzle 106, voltage source 108 and/or rotary actuator 103. In one implementation, controller 110 generates control signals causing one or more valves, mixers other components of material source 104 to adjust the composition of the electrospinning material supplied to nozzle 106 by source 104. By varying the composition, controller 110 may vary the composition and thickness of fibers 116 so as to control a thickness of distinct portions of the therapeutic carrier being formed upon collector 102.

In another implementation, controller 110 generates control signals to vary the operation or location of nozzle 106. For example, controller 110 may generate control signals adjusting an outlet size of nozzle 106 or may adjust the relative spacing of nozzle 106 relative to collector 102 to control the thickness of fibers 116 to control a thickness of distinct portions of the therapeutic carrier being formed upon collector 102.

In yet another implementation, controller 110 generates control signals to vary and control the operation of voltage source 108 and rotary actuator 1032 very and control thickness of distinct portions of the therapeutic carrier being formed upon collector 102. For example, in one implementation, controller 110 may increase or decrease the electrical potential between nozzle 106 and collector plate 102 to control the rate at which fibers 116 are deposited upon collector 102. Controller 110 may generate control signals to adjust the rate at which collector 102 is rotated by rotary actuator 103 to also control the rate or density at which fibers 116 are deposited upon collector 102.

As further shown by FIG. 3, in one implementation, system 100 may include a therapeutic source 118 configured to spray or otherwise coat a therapeutic upon fibers 116 after fibers 116 have been formed by before fibers 116 have been deposited upon collector 102. As a result, the therapeutic being provided by therapeutic source 118 is impregnated or integrated into fibers 116 as fibers 116 are layered upon collector 102 to form the and woven mesh of fibers forming the carrier. In other implementations, therapeutic source 118 bit alternatively deposit or coat the therapeutic upon the layers of fibers 116 upon collector 102 or upon the formed carrier after the carrier has been removed from collector 102.

Figure 4:
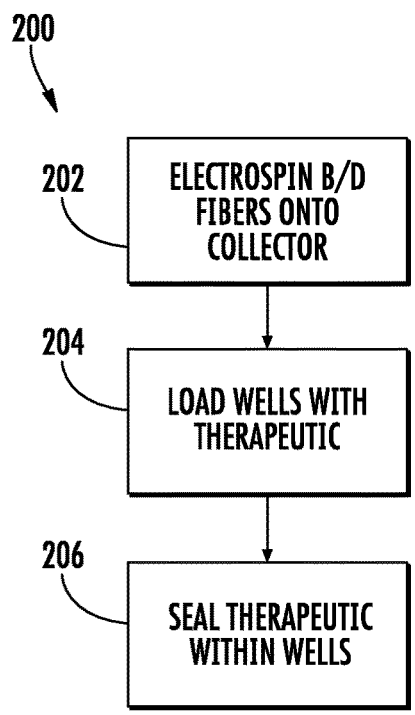
FIG. 4 is a flow diagram of an example method that may be at least partially carried out by the system of FIG. 3.

FIG. 4 is a flow diagram illustrating an example method 200 that may be at least partially carried out by system 100. As indicated by step 202, biodegradable fibers 116 are electrospun onto collector 102. The collector has floored recesses or protrusions that form a biodegradable layer having floored wells corresponding to the floored recesses or protrusions. As indicated by step 204, after the formed therapeutic carrier 22 (or another carrier) has been removed from collector 102 or while the carrier remains on collector 102, one or more selected wells 26 of carrier 22 are each loaded with a mass of therapeutic. As indicated by step 206, the therapeutic within each of the selected wells 26 is sealed. As noted above with respect to FIG. 2, in one implementation, a capping layer is secured over the carrier 22 and across the wells 26. In one implementation, multiple individual capping layers are independently applied and secured over selected wells 26 of carrier 22. In one implementation, the capping layer 30 comprised is laminated to the carrier 22. In one implementation, capping layer 30 is itself formed by electrospinning biodegradable fibers. In one implementation, capping layer 30 carries the same or a different therapeutic as containing wells 26.

Figure 5:
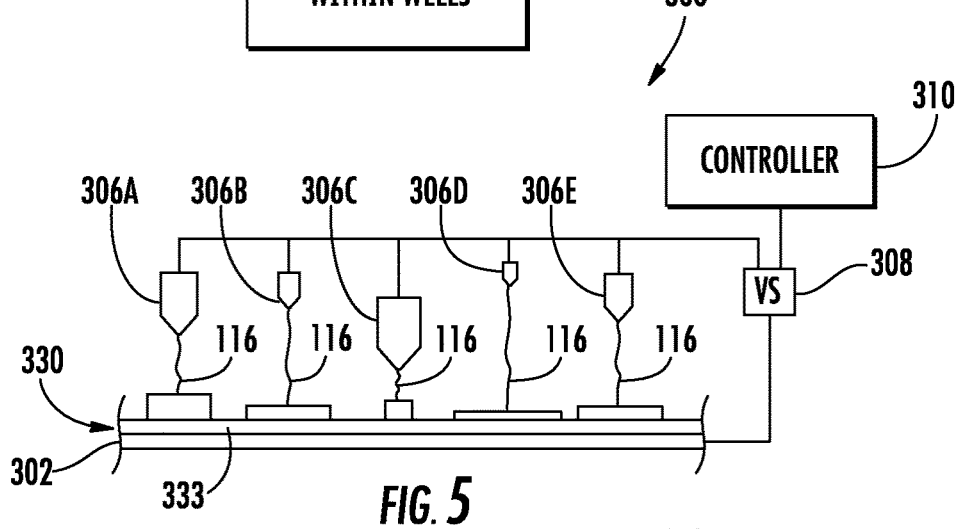
FIG. 5 is a schematic diagram of an example electrospinning system for forming an example capping layer.

FIG. 5 illustrates an example electrospinning system 300 for forming capping layer 330 having different regions of different thicknesses for use in sealing the therapeutic within wells 26 of therapeutic carrier 22. System 300 comprises collector 302, nozzles 306A, 306B, 306D and 306E (collectively referred to as nozzle 306), voltage source 308 and controller 310. Collector 302 comprises an electrically conductive member serving as a substrate upon which capping layer 330 is formed.

Nozzles 306 are connected to a single Electrospinning material source 104 or are each connected to dedicated independent Electrospinning material sources 104. Nozzles 306, like nozzles 106, are electrically charged to a distinct electoral potential with respect to collector 302 by voltage source 308. Voltage source 308 applies the distinct lexical potential across nozzles 306 and collector 302 such that nozzle 306 output electrospun fibers 116 which are deposited upon collector 302.

Controller 310 comprise one or more processing units, under the controller direction of instructions provided by a non-transitory computer-readable medium, that control the operation of the Electrospinning material sources 104, their associated nozzles 306 and/or voltage source 308. Controller 310 controls the differing thicknesses of the different regions or portions of capping layer 330. Such control may be achieved by controlling the composition of the electrospinning material applied by each of the nozzles 306, by controlling the spacing of the individual nozzles 306 relative to collector 302, by controlling the outlet size of nozzles 306 and/or by independently controlling the electrical potential between each nozzle 306 and collector 302.

In one implementation, one or more nozzles 306 are spaced a sufficient distance from collector 302 such that a large portion of collector 302 is substantially uniformly covered with electrospun fibers forming base 333 of capping layer 330. In yet another implementation, base 33 may be formed in other fashions and may be supported upon collector 302 to serve as a substrate for supporting the distinct thickness regions which are subsequently formed by electrospinning. In one implementation, controller 310 independently adjusts the spacing between nozzle 306 and collector 302 to vary the range or area upon the base 333 at which fibers 116 are deposited to vary a thickness of the individual regions. As noted above, in some implementations, the thickness of the different regions of capping layer 330 which extend over the individual wells 26 of carrier 22 may be controlled by also controlling composition of the electrospinning material provided by each of the material sources 104 for the different nozzles 306 as well as by varying the electrical potential between each of the novel 306 and collector plate 302. For example, in one implementation, voltage source 308 may establish a first illogical potential between nozzle 306A and collector 302 while establishing a second different electrical potential between nozzle 306C and collector 302 such that electrospun fibers are deposited upon collector 302 by the different nozzles at different rates to vary the thickness of the portions of capping layer 330 formed by such nozzles.

Figure 6:
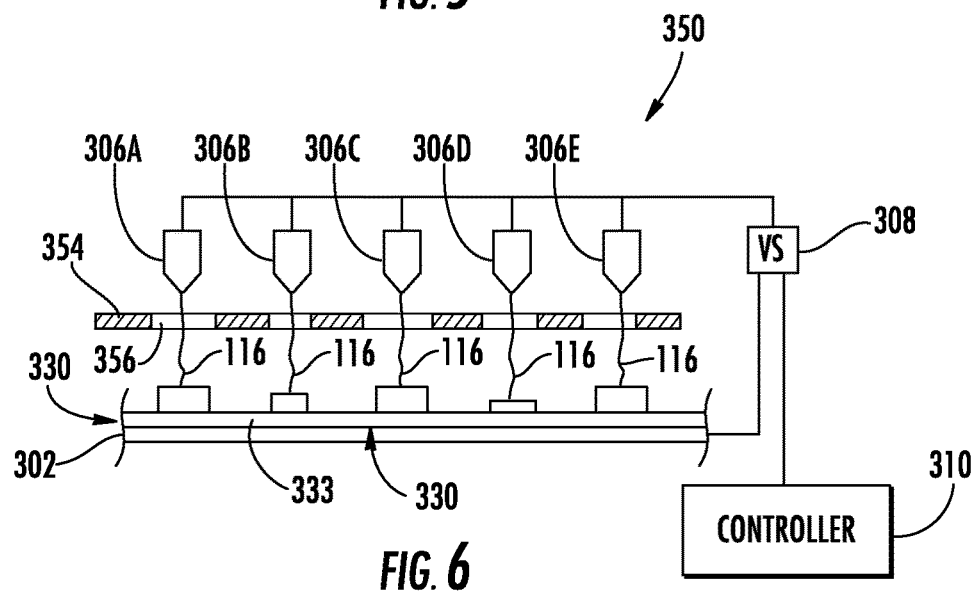
FIG. 6 is a schematic diagram of another example electrospinning system performing an example capping layer.

FIG. 6 schematically illustrates electrospinning system 350, an example implementation of electrospinning system 300. Electrospinning system 350 is similar to electrospinning system 300 except that electrospinning system 350 additionally comprises mask 354. Those remaining components of system 350 which correspond to components of system 300 are numbered similarly. Mask 354 comprises a dielectric or in selective plate position between nozzles 306 and collector 302. Mask 354 comprises a plurality of windows or apertures 356 through which the stream of fibers 116 pass from nozzles 306 onto collector 302. Apertures 356 are located so as to correspond to the location of the different thickness regions of capping layer 330 which correspond to the different wells 26 of therapeutic carrier 22. Apertures 356 serve to constrain the stream of fibers 116 to assist in controlling the area upon base 333 or upon collector 302 that the stream of fibers 116 become deposited. In one implementation, each aperture 356 has a selectively controllable varying size and/or shape. In one implementation, each aperture 356 has an associated actuator to adjust the size, wherein the actuator just size in response to signals from controller 310. In another implementation, system 350 comprises an actuator to raise and lower mask 354 to adjust the extent to which mask 350 constrains the stream of fibers 116 and thereby adjust the size or region in which fibers 116 are deposited.

Although mask 354 and collector 302 are illustrated as planar plates, in other implementations, collector 302 may alternatively comprise a rod or cylinder which rotates as fibers 116 are deposited thereon. In one implementation, collector 302 may comprise a rod or cylinder while mask 354 also comprises a tubular structure about the rod or cylinder of collector 302, wherein the tubular mask 354 includes one or more windows or apertures for constraining the stream of electrospun fibers 116 being deposited upon the collector 302.

Figure 7:
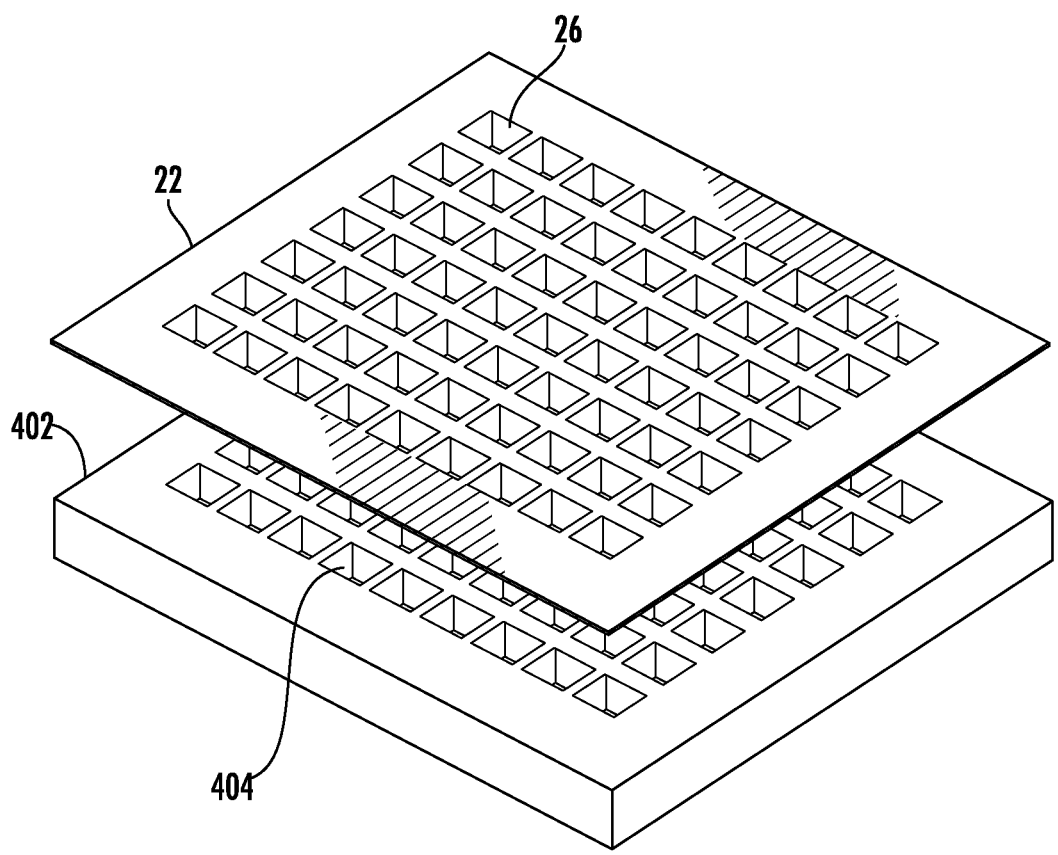
FIG. 7 is a perspective view of an example therapeutic carrier being separated from an example electrospinning collector plate.

FIG. 7 is a perspective view illustrating the separation of a formed therapeutic carrier 22 from an example collector 402. In the example illustrated, collector 402 comprises a an electrically conductive plate for being electrical connected to voltage source and having a grid or array of rectangular floored recesses or cavities 404 corresponding to the location of wells 26. In the example illustrated, the electrospun fibers 116 form upon the interior surfaces of each of recesses 404 to form the nonwoven mesh of such fibers 116 which forms carrier 22 with wells 16. In other implementations, collector 402 may alternatively comprise an electrically conductive plate having a grid or array of rectangular projections providing services upon which fibers 116 are deposited to form a nonwoven mat of fibers 116 such that the side of the nonwoven mat facing the projections include wells 16 when separated from collector 402.

Figure 8:
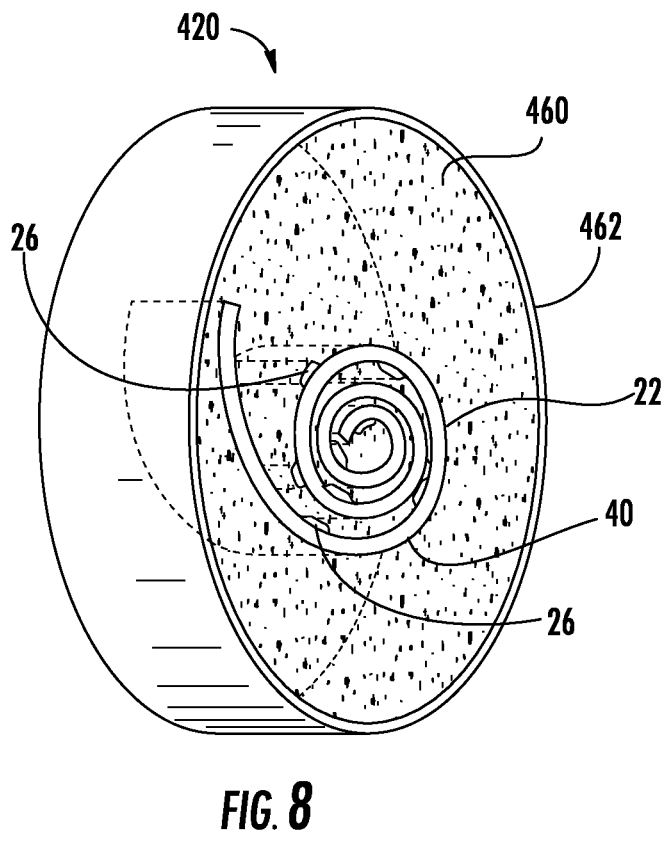
FIG. 8 is a sectional view of an example implantable device formed using the example therapeutic carrier of FIG. 7.

FIG. 8 is a section of illustrating therapeutic implantable device 420 formed using carrier 22. As shown by 8, once therapeutic masses 24 have been deposited in the selected wells 26 reference shown FIG. 7), therapeutic carrier 22 is wrapped such that the single panel of carrier 22 forms a plurality of spaced biodegradable layers 464 separating different therapeutic masses 24. For purposes of this disclosure, the term "wrapped" means that a single carrier 22 is bent, wound or otherwise shaped such that portions of carrier 22 face one another or overlap one another. In the example illustrated, carrier 22 is illustrated as being helically or spirally wound. In other words, carrier 22 comprises a plane curve cross-section generated by point moving around a fixed point while constantly receding from or approaching the fixed point to form a helix. Although illustrated as being spirally wound as a cylinder having a circular cross-section, concentric about a centerline or axis, in other implementations, carrier 22 may be spirally wound by one or more axes so as to have an elliptical cross-section or multi-lobed cross-section. In other implementations, carrier 22 may be "wrapped" in other fashions.

Because carrier 22 is wrapped, outermost therapeutic masses 24 on carrier 22 may be exposed and therefore released at times before innermost therapeutic masses 24 on carrier 22. As a result, the time at which a therapeutic is exposed and thereby delivered or released into a body may be predefined or controlled based upon the relative inner or outer positioning of the therapeutic mass 24 on the various windings of carrier 22. For example, a therapeutic mass 24 on an inner winding will be exposed and thereby released at a time much later than the release of a therapeutic mass 24 on an outer winding.

In the example shown FIG. 8, the therapeutic masses 24 are sealed within wells 26 by a biodegradable filler 460 which encapsulates the wound care 22 and contained therapeutic masses 24. Biodegradable filler 460 is itself contained within a biodegradable outer shell 462. In other implementations, capping layer 30 (or 330) may be laminated to or otherwise secured to carrier 22 to seal therapeutic masses 24 within wells 26 prior to carrier 22 and capping layer 30/330 being wound and encapsulated by filler 460 and surrounded by shell 462.

Figure 9:
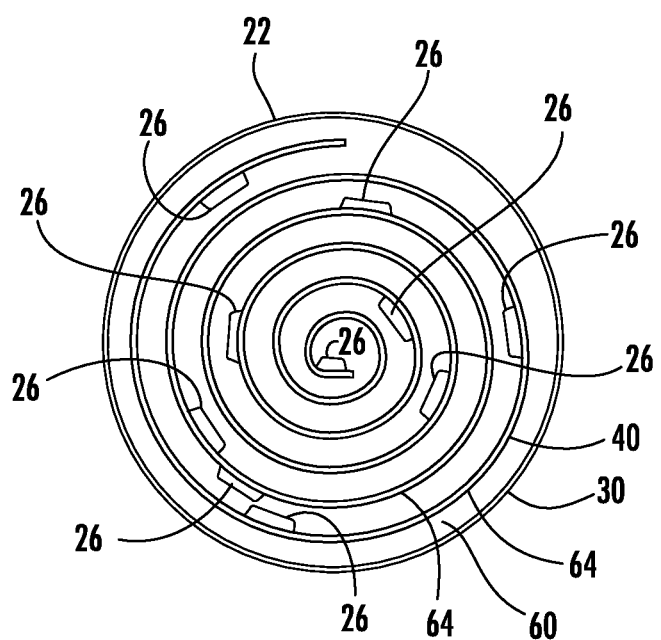
FIG. 9 is a sectional view of another example implantable device formed using the example therapeutic carrier FIG. 7.

FIG. 9 is a sectional view illustrating implantable device 520 formed from carrier 22. In the example illustrating FIG. 9, carrier 22 is loaded with therapeutic masses 24 and sealed by capping layer 30. The capped care 22 is then wound and secured in the wound state to form implantable device 520. As with implantable device 420, implantable device 520 releases therapeutic masses as carrier 22 and/or capping layer 30 biodegrades. Those wells 26 along the outer windings of carrier 22 biodegrade before those wells along the inner windings of carrier 22. As a result, the therapeutic masses contained in the outer winding wells 26 are released prior to the therapeutic masses contained in the inner winding wells 26. As a result, like implantable device 420, implantable device 520 facilitates a timed release of therapeutic masses.

The timed release of therapeutic masses 24 may be adjusted or controlled by adjusting factors such as how tight carrier 22 is wrapped or wound, the number of wraps or windings and the folding pattern (with respect to the example in FIG. 3). Identical carriers 22 having identical patterns of deposit therapeutics may be provided with different time release characteristics by simply adjusting any of the aforementioned factors. In other implementations, the timed release of therapeutics (the timing at which therapeutics are released) may be adjusted further by adjusting the pattern at which therapeutic masses 24 are deposited within particular wells 26 prior to such wrapping.

Figure 10:
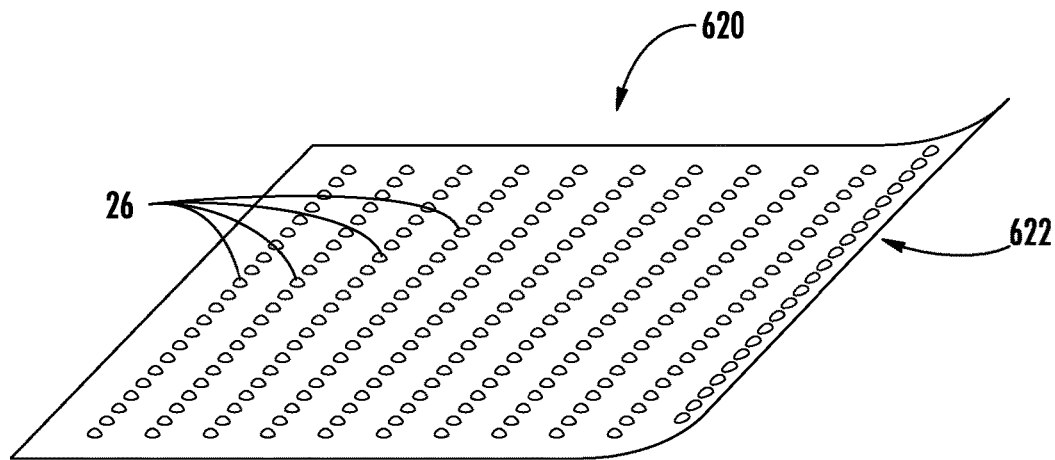
FIG. 10 is a perspective view of another example carrier formed from electrospun biodegradable fibers.
Figure 11:
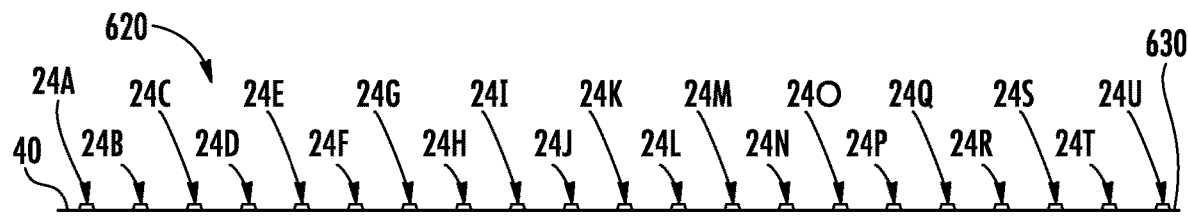
FIG. 11 is a side view of the therapeutic carrier of FIG. 10 with wells filled with therapeutic masses and sealed.
Figure 12:
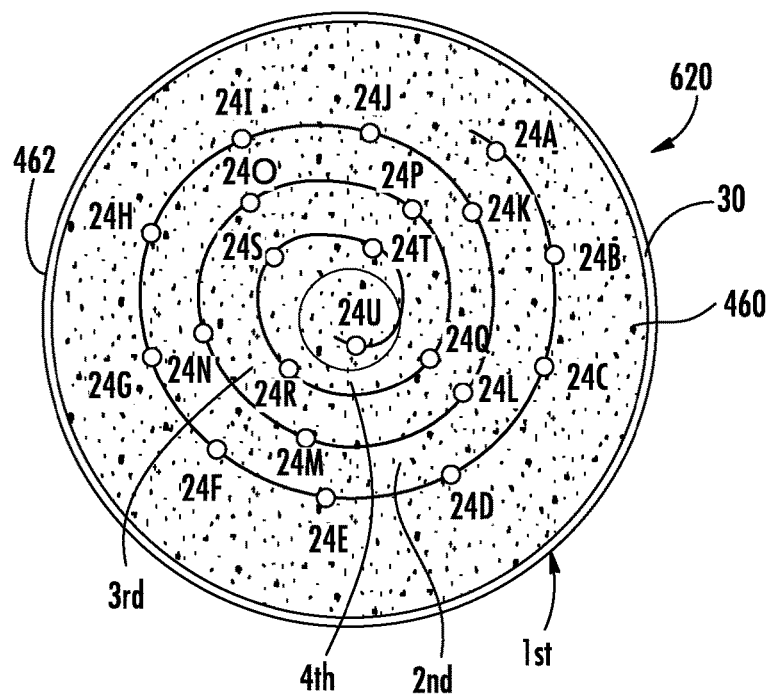
FIG. 12 is a sectional view of an example implantable device formed from the loaded and sealed therapeutic carrier of FIG. 11.

FIGS. 10-12 illustrate the formation of implantable device 620 (shown in FIG. 12). FIG. 10 illustrates carrier 622 comprising a multitude of individual wells 26 which are filled with therapeutic masses 24 (referenced in FIG. 11). In one implementation, the filled wells 26 are covered and sealed by capping layer 630.

FIG. 12 illustrates the winding of carrier 622 with the sealed wells 24 filled with therapeutic masses 26. FIG. 12 further illustrates the wound carrier 622 encapsulated within a biodegradable liquid or solid filler 460 which is contained within the biodegradable outer shell 462.

Figure 13:
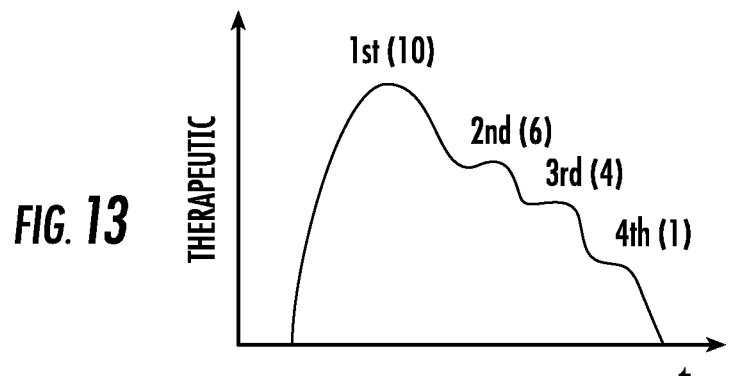
FIG. 13 is a graph illustrating the timed release of therapeutics from the implantable device of FIG. 12.

FIG. 13 is a graph illustrating the release of therapeutics over time with implant 620 as shown by FIG. 12, the outermost winding has a largest circumference and therefore has the largest number of rows of therapeutics. The innermost winding has the smallest circumferential length, having the fewest number of rows of therapeutics. In the example illustrated, the outermost winding has 10 rows of therapeutics, the next inner winding has 6 rows of therapeutics, the next inward winding has 4 rows of therapeutics and the innermost winding or portion of carrier 22 has just 1 row of therapeutics. As implant 620 and the layers biodegradable material between the various windings breaks down, the therapeutics on the windings are sequentially exposed, sequentially releasing therapeutics, beginning with the outermost winding and finishing with the innermost winding. As shown by FIG. 13, implant 620 achieves a timed release of therapeutics wherein the largest amount of therapeutics is initially released and subsequent release of therapeutics are stepwise reduced over time.

Figure 14:
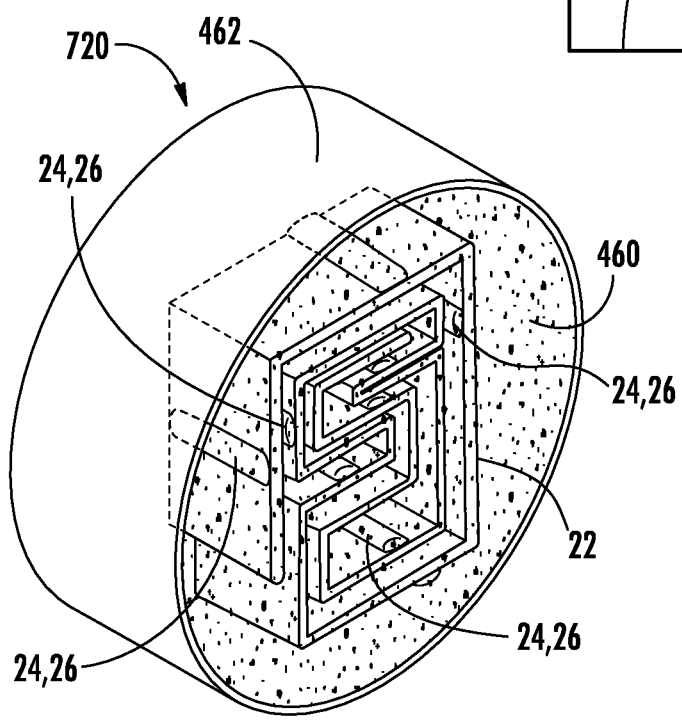
FIG. 14 is a perspective view of another example implantable device formed from the loaded and sealed therapeutic carrier of FIG. 11.

FIG. 14 illustrates implantable device 720. Implant or implantable device 720 is similar to implantable device 420 except that carrier 22 with therapeutic masses 24 is wrapped in a different manner. Instead of being spirally wound, carrier 22 is folded. In contrast to being spirally wound wherein carrier 22 is always extending inwardly or outwardly circumferentially about a centerline or axis, carrier 22 is wrapped wherein carrier 22 extends in opposite directions at times. Although illustrated as being folded in the form of a square or rectangular cross-sectional shape, in other implementations, carrier 22 may be wrapped or folded with other folding patterns so as to have other cross-sectional shapes.

Figure 15:
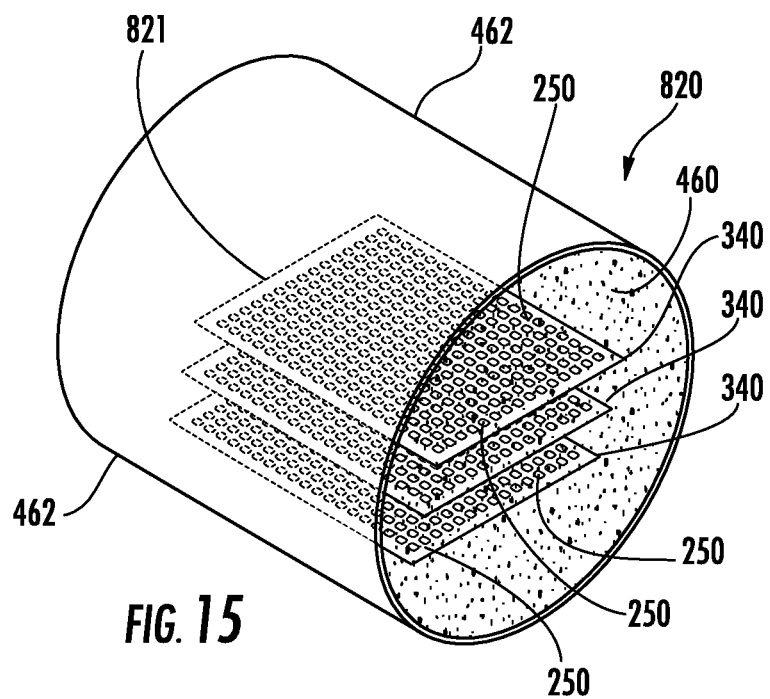
FIG. 15 is a perspective view of another example implantable device formed from the loaded and sealed therapeutic carrier of FIG. 11.

FIG. 15 illustrates implantable device 820. Implantable device 820 is similar to implantable device 720 except that carrier 22, once loaded with therapeutic masses 24 and sealed by capping layer 30 (or 330) is severed into distinct panels 721 which are layered or stacked upon one another and are encapsulated in the stacked arrangement by biodegradable filler 460 which is contained within biodegradable outer shell 462. In yet another implementation, cares 24 are properly sized such that cares 22 may be stacked upon one another in whole, without being severed into portions. As with implantable device 720, implantable device 721 provides a timed release of therapeutics based upon the time consumed two biodegrade different portions of the one of more carriers 22 and/or capping layers 30. The innermost layers or innermost carriers of the stack released therapeutics at a time following the release of therapeutics by the outermost (top and bottom) layers of the stack formed by carriers 22. The center most wells 26 having therapeutic masses 24 release their therapeutics at a time later than the wells 26 along the perimeter of each of the layers or carriers 22.

Figure 16:
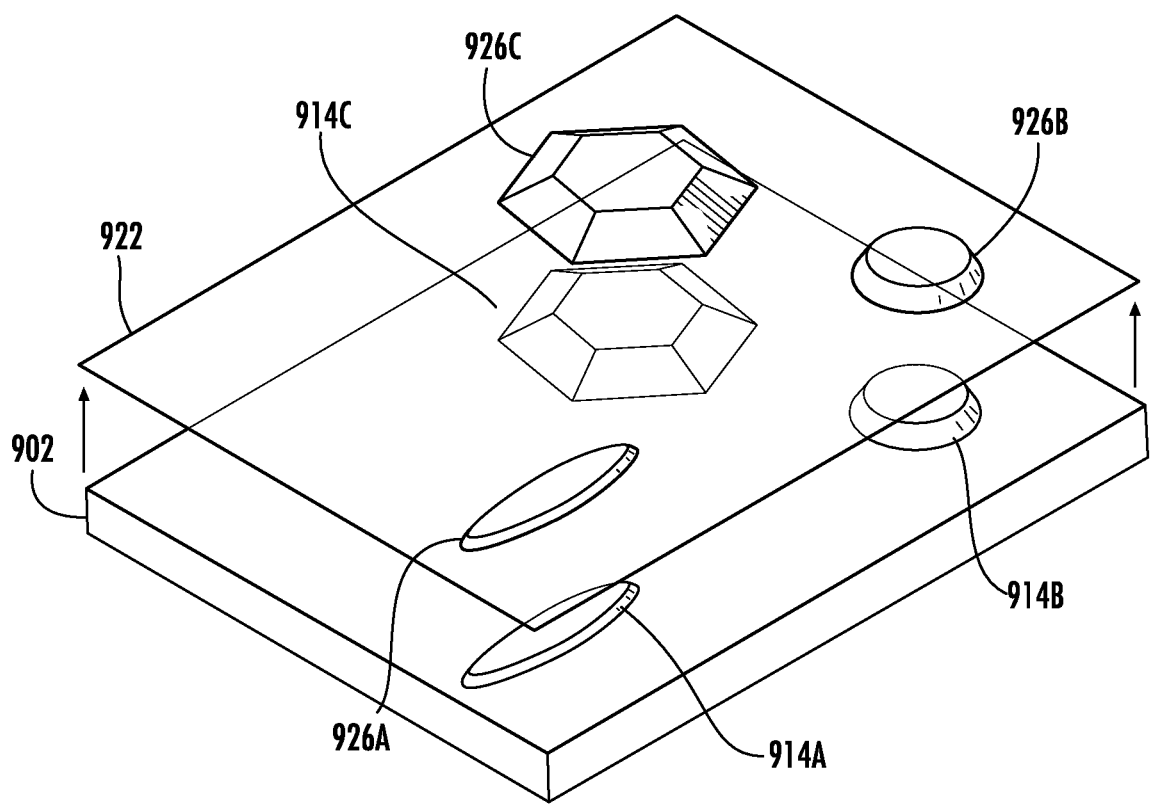
FIG. 16 is a perspective view of an example therapeutic carrier being separated from an example collector.

FIG. 16 is a perspective view illustrating separation of an example therapeutic carrier 922 formed from the example collector plate 902. Collector plate 902 illustrates three differently shaped projections 914A, 914B, 914C providing surfaces upon which electrospun fibers 116 are applied by electrospinning to form carrier 922. As a result, upon separation and rotation of carrier 922 from collector 902, carrier 922 comprises three differently shaped wells 926A, 926B, 926C. As shown by 16, the size and shape of wells 926 may be customized to contain different amounts of therapeutics.

Figure 17:
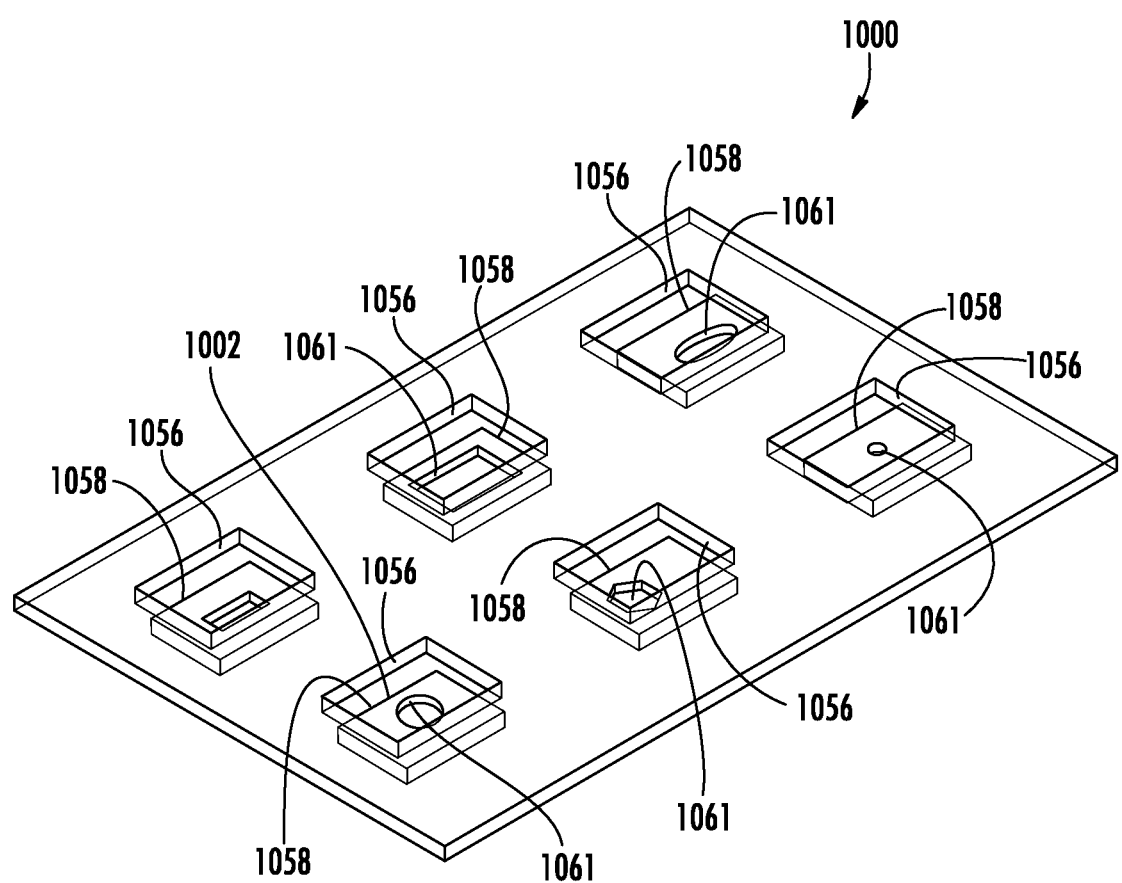
FIG. 17 is a perspective view of another example electrospinning system.

FIG. 17 is a perspective view illustrating electrospinning system 1000. Electrospinning system 1000 is similar to electrospinning system 100 except that system 1000 comprises collector 1002 in lieu of collector 102, comprises a plurality of independently operable nozzles similar to nozzles 306 (shown and described above with respect to FIGS. 5 and 6) and further includes masking plate 1054. Those remaining components of system 1000 are numbered similarly or are shown in FIG. 3.

Collector 1002 comprises an electrically conductive plate having distinct regions 1058, each region 1058 comprising a recess 1061 in the shape of a to be formed well 26. In another implementation, each region 1058 may comprise a projection in the negative impression shape of a to be formed well 26. Each region receives electrospun fibers 116 from a corresponding associated overhead nozzle 306 to form an individual therapeutic carrier, each of the individual carriers are not connected to other carriers formed on collector 1002.

Masking plate 1054 comprises a dielectric or insulative plate supported between collector 1002 and the overhead nozzle 306 assigned each of regions 1058. Passing plate 1054 comprises apertures 1056 which correspond to each region 1058. As with apertures 356 of system 350 described above, apertures 1056 constrain the stream of electrospun fibers 116 to control the dispersion of such fibers upon collector 1002 and upon the associated particular region 1058. In other implementations, masking plate 1054 may be omitted, wherein regions 1058 are severed from one another or wherein the spacing of knowledge 306 relative collector 1002 is utilized to control the dispersion of fibers 116 upon collector 1002.

Figure 18:
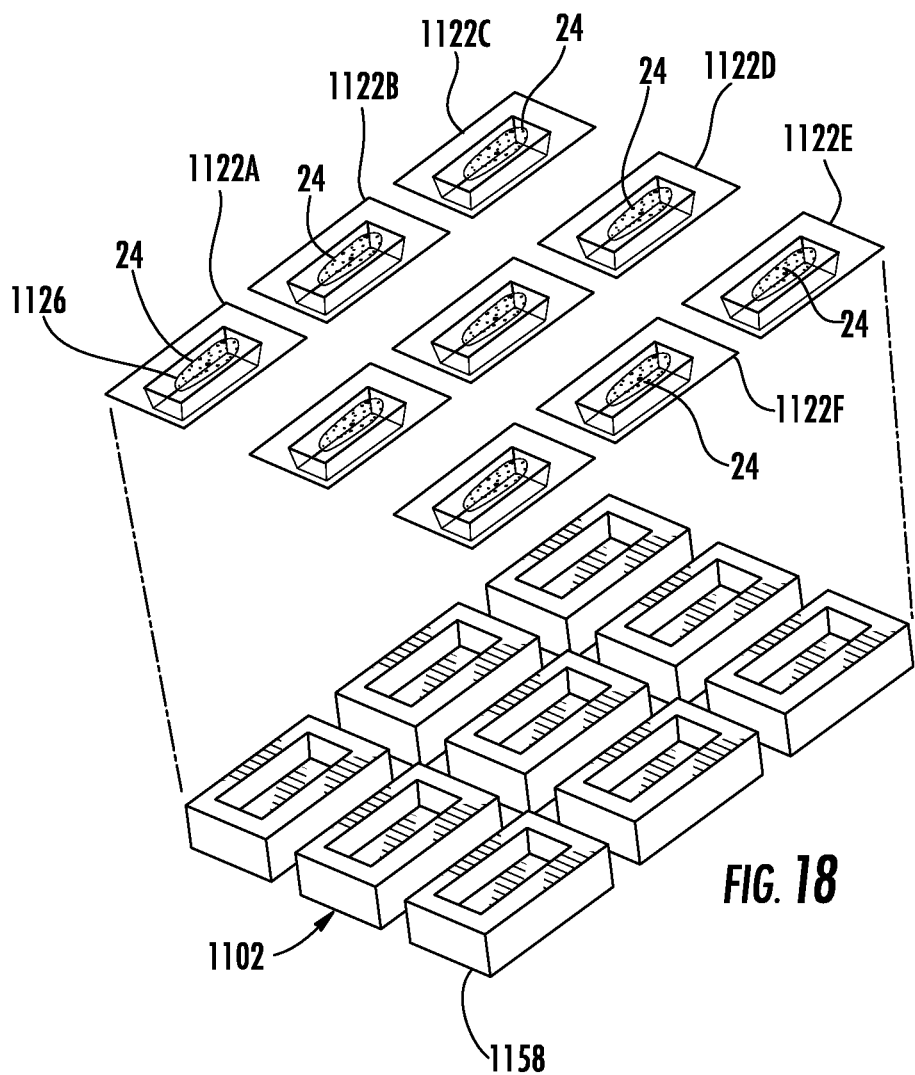
FIG. 18 is a perspective view of example independent therapeutic carriers being separated from an electrospinning collector and being loaded with therapeutic masses.
Figure 19:
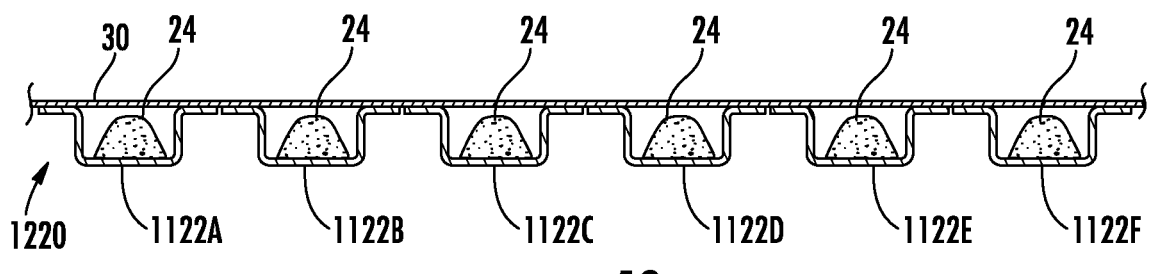
FIG. 19 is a sectional view of an example implantable device formed using the independent and distinct loaded therapeutic carriers of FIG. 18.

FIG. 18 illustrates a number of individual and distinct therapeutic carriers 1122A-F (collectively referred to as carriers 1122) separated from regions 1158 of collector 1102. FIG. 18 further illustrates the loading of a well 1126 of one of carriers 1122 with a therapeutic mass 24. Because each of carriers 1122 shown in FIG. 18 may be independently formed using different electrospinning materials from different nozzles 306, different therapeutics may be incorporated into the electrospun fibers of different carriers 1122 despite solvent or other incompatibility constraints. As shown by FIG. 19, the individual carriers electrospun from fibers incorporating therapeutics with incompatible solvent constraints are joined as part of a single larger implantable device 1220 for being implanted or for being wound as described above. In one implementation, the wells 1126 of the independent carriers 1122 loaded with the same or different solvents are sealed by single capping layer 30 that is laminated or otherwise secured across the top of each of wells 1126. Because implantable device 1220 is formed from a plurality of independently formed carriers 1122 which are joined together by a single capping layer 30, the individual carriers 1122 may be preloaded with therapeutic masses 24 and stored for subsequent use, facilitating modular customization of implantable device 1220 by selectively combining and joining different combinations of different preloaded carriers 1122 with capping layer 30. In another implementation, the individual preloaded tears 1122 may be individually sealed, wherein the preloaded and sealed carriers 1122 are joined to one another by common biodegradable interconnecting substrate or panel which is left flat or which is wound or rolled as described above.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A therapeutic implantable device comprising:
a biodegradable layer comprising electrospun fibers forming wells;
a mass of a therapeutic within each of the wells, each mass of the therapeutic being entirely contained within each of the wells; and
a capping layer sealing the mass of the therapeutic within a capped volume of each of the wells and isolating the capped volume of each of the wells from the capped volume of others of the wells, wherein the mass of therapeutic has a volume different than the capped volume.

2. The therapeutic implantable device of claim 1, wherein the electrospun fibers have incorporated therein a second therapeutic different than the therapeutic.

3. The therapeutic implantable device of claim 2, wherein the electrospun fibers of the capping layer have incorporated therein a third therapeutic different than the therapeutic and the second therapeutic.

4. The therapeutic implantable device of claim 1, wherein the capping layer comprises electrospun fibers.

5. The therapeutic implantable device of claim 4, wherein the capping layer has a first thickness over a first one of the wells and a second thickness, different than the first thickness, over a second one of the wells.

6. The therapeutic implantable device of claim 4, wherein the electrospun fibers of the capping layer have incorporated therein a second therapeutic different than the therapeutic.

7. A therapeutic implantable device comprising:
a biodegradable layer comprising electrospun fibers forming wells;
a mass of a therapeutic within the wells; and
a biodegradable outer shell, wherein the biodegradable layer is coiled within the biodegradable outer shell.

8. A therapeutic implantable device comprising:
a biodegradable layer comprising electrospun fibers forming wells; and
a mass of a therapeutic within the wells; and
a biodegradable outer shell, wherein the biodegradable layer is folded within the biodegradable outer shell.

9. A biodegradable therapeutic carrier comprising:
a layer of biodegradable electrospun material; and
floored wells formed by the layer to contain therapeutic, wherein a first one of the floored wells has a first density or thickness of electrospun material and wherein a second one of the floored wells has a second density or thickness of electrospun material less than the first density or thickness.

10. The therapeutic implantable device of claim 1, wherein the biodegradable layer comprises a sheet having a flat upper surface and a two dimensional array of the wells extending from the flat upper surface.

11. The therapeutic implantable device of claim 1, wherein the biodegradable layer and the capping layer are wrapped to overlap themselves so as to form at least three overlapping layers comprising a first layer, a second layer and a third layer, the second layer being between the first layer and the third layer, the third layer overlapping the first layer and the second layer in a radial direction from an axial centerline of the wrapped biodegradable layer.

12. A therapeutic implantable device comprising:
a biodegradable layer comprising electrospun fibers forming wells;
a mass of a therapeutic within each of the wells, each mass of the therapeutic being entirely contained within each of the wells; and
a capping layer sealing the mass of the therapeutic within a capped volume of each of the wells and isolating the capped volume of each of the wells from the capped volume of others of the wells, wherein the mass of therapeutic has a volume different than the capped volume, wherein the biodegradable layer and the capping layer are wrapped to overlap themselves so as to form at least three overlapping layers comprising a first layer, a second layer and a third layer, the second layer being between the first layer and the third layer, the third layer overlapping the first layer and the second layer in a radial direction from an axial centerline of the wrapped biodegradable layer, wherein the biodegradable layer and the capping layer are wrapped to overlap themselves and wherein innermost windings of the wrapped biodegradable layer and capping layer defining an inner winding volume therebetween, the therapeutic implantable device further comprising a biodegradable fill material filling the inner winding volume.

13. The therapeutic implantable device of claim 1, wherein the capping layer is laminated to the biodegradable layer.

14. The therapeutic implantable device of claim 1, wherein each of the wells has a controlled volume.

15. The therapeutic implantable device of claim 1, wherein the wells comprise a polygonal well having flat floor and a plurality of sidewalls.

16. The therapeutic implantable device of claim 1, wherein the biodegradable layer comprises a planar sheet having a flat upper surface and wherein each of the wells extends into the flat upper surface with a top of each well adjacent the flat upper surface and a floor of each well distant the flat upper surface.

17. A biodegradable therapeutic carrier comprising:
a well comprising electro spun fibers, the well comprising:
  a floor;
  sidewalls extending from the floor, the sidewalls comprising a first end joined to and adjacent the floor and a second end distant the floor; and
  a flat rim extending outwardly from the second end of the sidewalls, wherein the flat rim extends about an uncovered mouth opening into an empty interior of the well, the uncovered mouth providing a passage through which the empty interior of the well receives a mass of therapeutic;
a second well comprising electro spun fibers, the second well comprising:
  a second floor;
  second sidewalls extending from the second floor, the second sidewalls comprising a first end joined to the floor and a second end distant the floor; and
  a second flat rim extending outwardly from the second end of the sidewalls;
a first mass of therapeutic within the well;
a second mass of therapeutic within the second well; and
a continuous capping layer continuously extending across the mouth to cover the mouth and directly joined to and directly connected to the flat rim and the second flat rim to connect the well and the second well, the capping layer sealing the first mass of therapeutic within the well and the second mass of therapeutic within the second well.

18. The biodegradable therapeutic carrier of claim 17, wherein the first well and the second well are separate structures joined solely by the capping layer.

19. The biodegradable therapeutic carrier of claim 17, wherein the continuous capping layer forms a capped volume within the well and wherein the first mass of therapeutic within the well has a volume different than the capped volume.

20. The biodegradable therapeutic carrier of claim 17, wherein the well has an interior having a first shape and wherein the mass of therapeutic comprises a solid having a second shape different than the first shape.

21. The biodegradable therapeutic carrier of claim 17, wherein the first mass of therapeutic within the well comprises a liquid.

* * * * *